United States Patent
Meyer et al.

(10) Patent No.: US 6,814,482 B2
(45) Date of Patent: Nov. 9, 2004

(54) METHOD FOR DISPERSING RED AND WHITE BLOOD CELLS

(75) Inventors: Robert J. Meyer, Penfield, NY (US); Christine J. Tarnawskyj, Webster, NY (US)

(73) Assignee: Xerox Corporation, Stamford, CT (US)

( * ) Notice: Subject to any disclaimer, the term of this patent is extended or adjusted under 35 U.S.C. 154(b) by 147 days.

(21) Appl. No.: 10/219,623

(22) Filed: Aug. 15, 2002

(65) Prior Publication Data

US 2003/0012078 A1 Jan. 16, 2003

Related U.S. Application Data

(63) Continuation-in-part of application No. 09/699,804, filed on Oct. 30, 2000, now abandoned.

(51) Int. Cl.$^7$ ............................................. B01F 11/02
(52) U.S. Cl. .......................................... 366/116; 601/2
(58) Field of Search ............................. 601/2; 366/108, 366/110–118, 120–122, 127

(56) References Cited

U.S. PATENT DOCUMENTS

| | | | | |
|---|---|---|---|---|
| 3,352,303 A | * | 11/1967 | Delaney | 601/2 |
| 5,004,165 A | | 4/1991 | Landa et al. | 241/21 |
| 5,048,762 A | | 9/1991 | Landa et al. | 241/21 |
| 5,078,504 A | | 1/1992 | Landa et al. | 366/118 |
| 5,223,368 A | | 6/1993 | Ciccarelli et al. | 430/110 |
| 5,399,158 A | * | 3/1995 | Lauer et al. | 604/22 |
| 5,431,663 A | * | 7/1995 | Carter | 606/128 |
| 5,492,788 A | | 2/1996 | Denton et al. | 430/137 |
| 5,524,620 A | * | 6/1996 | Rosenschein | 600/407 |
| 6,432,604 B1 | * | 8/2002 | Meyer et al. | 430/137.1 |

OTHER PUBLICATIONS

M.A. Biot, *Theory of Propagation of Elastic Waves in a Fluid–Saturated Porous Solid*, Mar. 1956, 168, 179, ibid.

M.A. Biot, *Mechanics of Deformation and Acoustic Propagation in Porous Media*, Apr. 1962, 1482.

D.L. Johnson, T.J. Plona and H. Kojima, *Probing Porous Media with First and Second Sound. II. Acoustic Properties of Water–Saturated Porous Media*, Mar. 1994, 115.

T.J. Plona, R. D'Angelo and D.L. Johnson, *Velocity and Attenuation of Fast, Shear and Slow Waves in Porous Media*, 1991, 1233–1239.

S. Torquato, *Random Heterogeneous Media: Microstructure and Improved Bounds on Effective Properties*, Feb. 1991, 37.

J.E. White, *Seismic Waves: Radiation, Transmission and Attenuation*, 1965, 70.

W.A. Gray, *The Packing of Solid Particles*, 1968, 34.

* cited by examiner

*Primary Examiner*—David Sorkin
(74) *Attorney, Agent, or Firm*—Lloyd F. Bean, II

(57) ABSTRACT

A method and apparatus for dispersal of aggregates of red and white blood cells and platelets. The present invention employs a sonic or ultrasonic device to efficiently breakup aggregates of red and white blood cells and platelets by driving the ultrasonic signal over a small range of frequencies around the acoustic slow wave frequency of the agglomerate. At this frequency, the fluid vibrates out of phase with the solid and is forced out through the pore structure in the agglomerate.

17 Claims, 4 Drawing Sheets

METHOD FOR DISPERSING RED AND WHITE BLOOD CELLS

Figure 1:
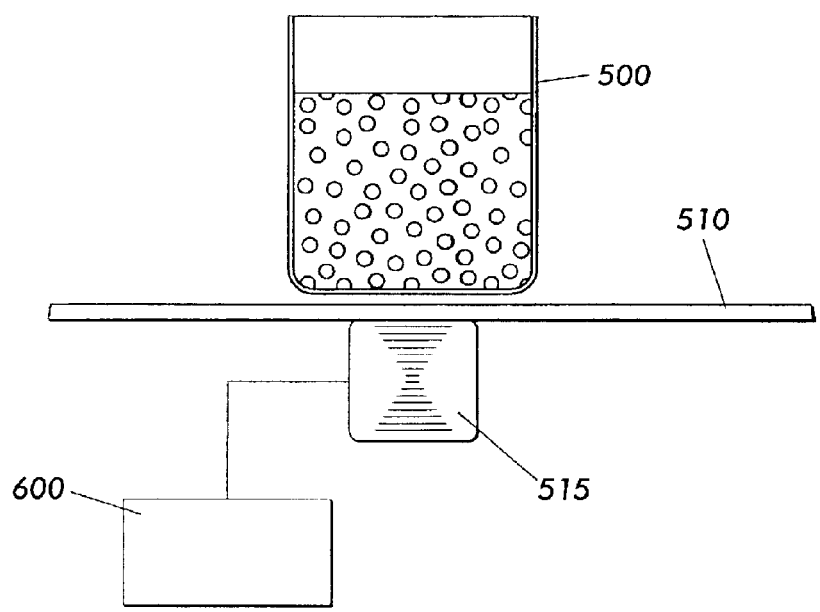
Figure 2:
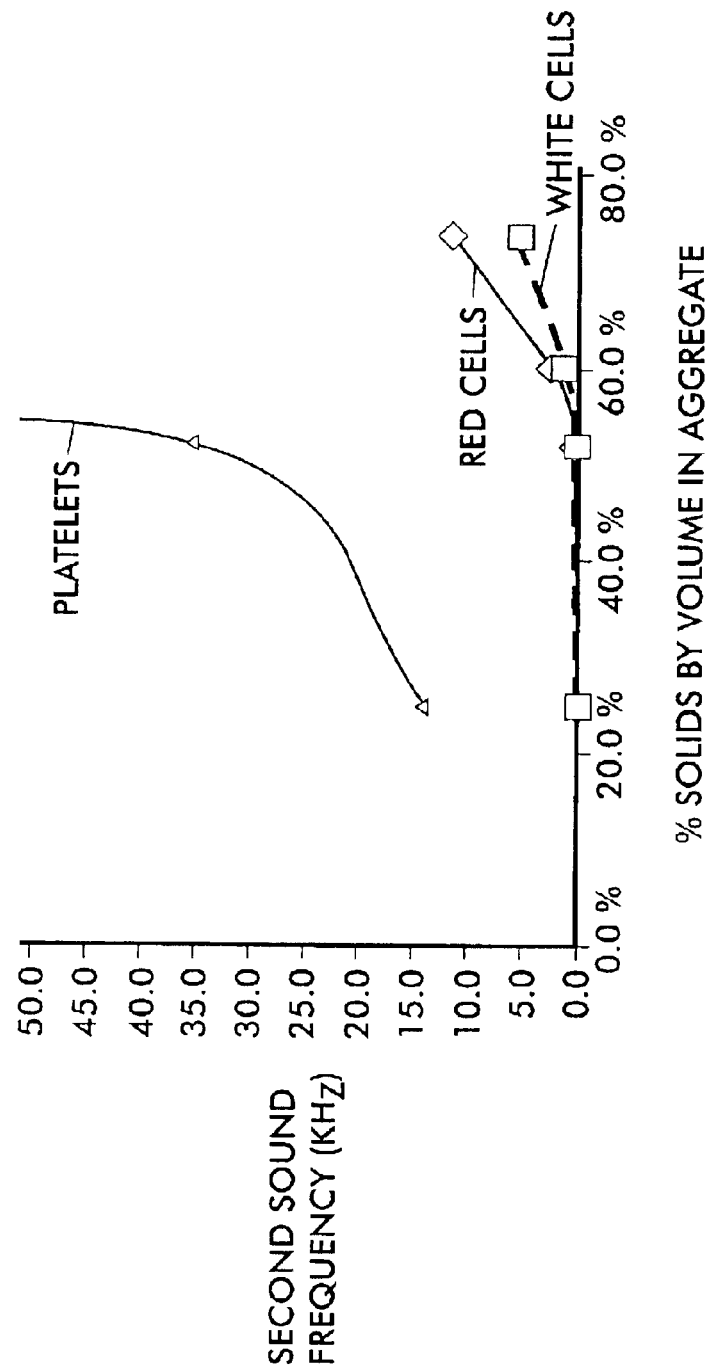
Figure 3:
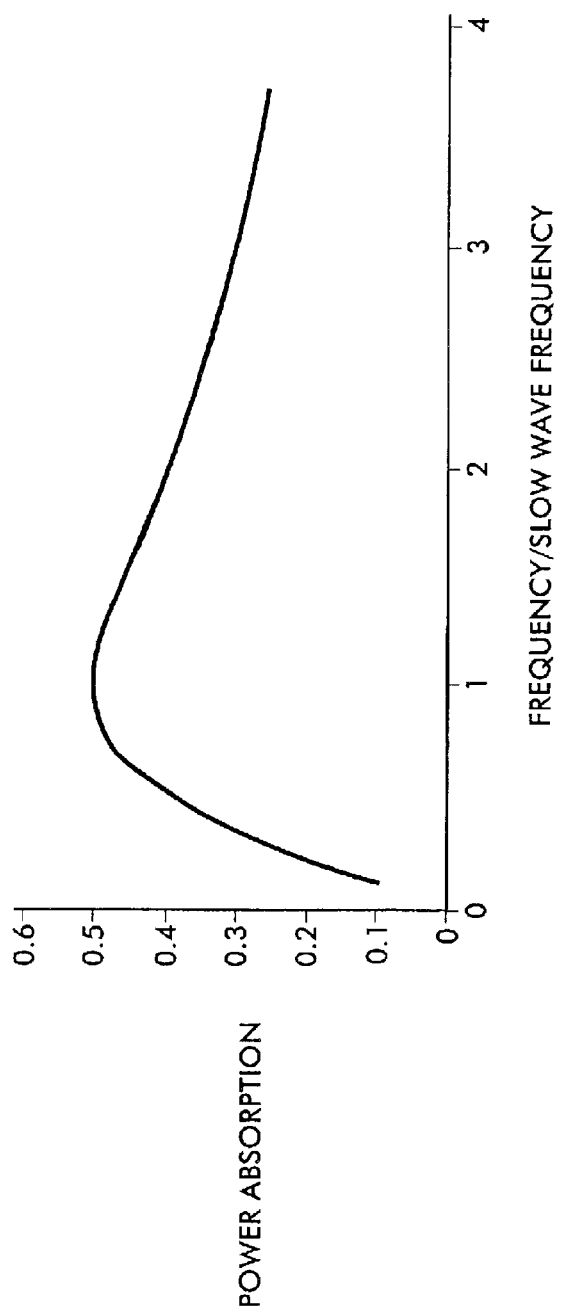
Figure 4:
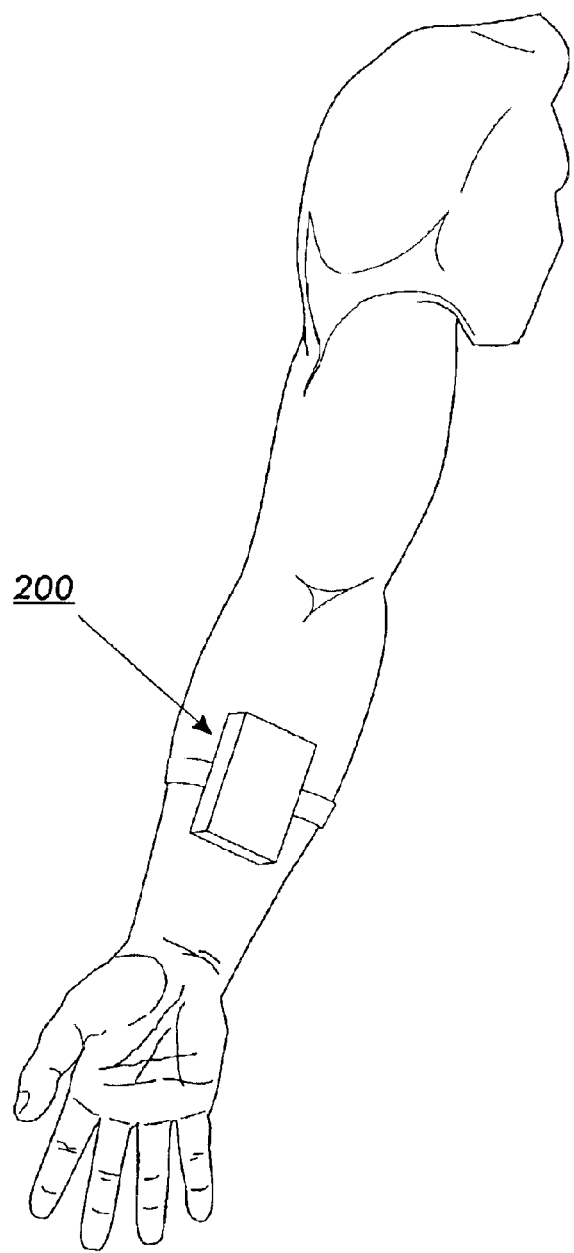

This application is a continuation-in-part of U.S. patent application Ser. No. 09/699,804, filed Oct. 30, 2000 now abandoned.

This invention is generally directed to a method and apparatus for dispersal of aggregates of red and white blood cells and platelets. The present invention employs a sonic or ultrasonic device to efficiently breakup aggregates of red and white blood cells and platelets by driving the ultrasonic signal over a small range of frequencies around the acoustic slow wave frequency of the agglomerate. At this frequency, the fluid vibrates out of phase with the solid and is forced out through the pore structure in the agglomerate.

Compressional ultrasonic waves Interact with particle aggregates, whether they are aggregates of blood cells or aggregates of pigment particles, in a limited number of ways. Each way can have its own set of technological advantages and disadvantages that make it suitable for some applications, and unsuitable for others. For example, the pressure within an ultrasonic wave is at a maximum at one location within the wave, called the peak, and at a minimum ½ wavelength away, at the valley. There is a stress exerted on a particle aggregate due to this difference in pressure. If that stress exceeds the yield stress of the aggregate, particle breakup occurs. However, for a compressional wave velocity of 1520 m/sec (velocity of sound in water) and a frequency of 10,000 Hz the wavelength is 15.2 cm. This approach is not appropriate for breaking up blood cell aggregates.

Another approach to breaking up particle aggregates is by inducing cavitation. If the amplitude of the pressure wave is sufficient, and the frequency is in the appropriate optimum range, dissolved gases can be pulled from solution to form microscopic bubbles, which grow and then collapse under the influence of the pressure wave. The dynamics of this process is governed by the Kirkwood-Bethe equation. For fluids such as water and blood serum, the maximum for cavitation generation frequency occurs around 20 kHz, with an overtone at around 40 kHz. Required pressure amplitudes are on the order of a few tenths of an atmosphere. However, when cavitation bubbles collapse pressures on the order of $10^4$ atmospheres can be generated. These stresses do very well in breaking up particle aggregates. However, these pressures far exceed the yield stresses of cell membranes, and so cavitation can do considerable damage to biological specimens, including blood.

Therefore there is a need for a method and apparatus for dispersal of aggregates of red and white blood cells which overcomes the beforementioned problems There is provided a method for dispersing aggregates in a liquid medium including blood the method comprising: holding aggregates in said liquid medium in a vessel; applying a predefined acoustic slow wave frequency near said vessel for separating the aggregates in said liquid medium, said applying includes selecting a type aggregates to be dispersed in said liquid medium, determining said predefined acoustic slow wave frequency of said selected aggregates. Wherein determining said predefined said acoustic slow wave frequency includes calculating said predefined said acoustic slow wave frequency by the following equation:

$$f_c=\eta\{S_v^2(1-\phi)^2\}/(2\pi B\,\phi^2\,\rho_f)$$

Where $f_c$ is the acoustic slow wave frequency, $\eta$ is the fluid viscosity, $S_v$ is the primary particle surface area per unit volume of the aggregate, $\phi$ is the aggregate porosity, $\rho_f$ is the fluid viscosity, and B is a phenomenological constant.

The aggregates include red blood cells, white blood cells or platelets.

The method further comprising determining and applying a second predefined acoustic slow wave frequency as said primary particle surface area per unit volume of the aggregate changes. And, repeating said determining and applying steps until said primary particle surface area per unit volume of the aggregates reaches a selected primary particle surface area per unit volume of the aggregates.

The accompanying FIG. 1 is a schematic of a system wherein blood aggregates in a container or in bags can be dispersed in accordance with the invention.

FIG. 2 is a graph of acoustic slow wave frequencies for red blood cells and for white blood cells. Blood cell agglomerates can be redispersed by the present invention.

FIG. 3 is a graph of power absorption versus acoustic slow wave frequencies.

FIG. 4 illustrates a hand held unit to break up blood clots using the principles of the present invention.

DETAILED DESCRIPTION OF THE INVENTION

The present invention improves the efficiency of ultrasonic aggregate dispersion techniques by tailoring the ultrasonic frequency specifically to the nature of the aggregates that are to be dispersed. As discussed in more detail below, aggregate breakup is possible by utilizing ultrasonic waves at or near a specific frequency called the acoustic slow wave or second sound frequency. At this point fluid is forced to move through the pore spaces and necks within each individual particle aggregate. This fluid motion exerts viscous drag forces on the particles, especially in the region of particle-particle contact points, and acts to break the adhesive particle-particle bonds within the solid frame of the aggregate. Thus, these forces act over an entirely different distance range, and via a different mechanism, than the forces acting between pressure maxima and minima in an ultrasonic wave. The acoustic slow wave method of the present invention makes use of the realization that the propagation of sound through porous media containing a viscous fluid has different modes of motion which may be excited at different frequencies.

Typical aggregate sizes may vary from 10 to several hundred primary particles, or from 1 micron to 200 microns in average volume diameter prior to sonification. The sonification comprises applying the ultrasonic signal for a period of time of from about 0.01 seconds (e.g., 100 cycles at a 10 kHz slow wave frequency) to several minutes.

In an embodiment of the invention, the acoustic slow wave mode is used to break up particle aggregates in which the physical properties of the particle aggregates and their pore fluid is known. The frequency of the ultrasound is set by of knowing the following information: the particle size, some notion of their packing fraction (or percent solids in the aggregates), and the viscosity and density of the pore fluids. From this information, as discussed below, we can estimate the acoustic slow wave frequency, i.e., the frequency that we want to apply to the suspension of fluid and fluid-saturated aggregates:

$$f_c=\eta\phi/(2\pi k\rho_f) \quad (1)$$

where $\eta$ is the fluid viscosity, $\phi$ is the aggregate porosity, k is the aggregate permeability, and $\rho_f$ is the fluid density.

By applying this frequency ultrasonic signal, or white ultrasonic energy around the acoustic slow wave frequency we can redisperse a coagulated suspension of particles, or prevent coagulation of an initially dispersed suspension.

The ultrasonic applying means for applying an acoustic slow wave in the present invention can be, for example, Ultrasonic probes vibrating at or around the slow wave frequency can be inserted into containers containing aggregates to be dispersed;. Container 500 can be placed on an ultrasonic stage 510 using a piezoelectric vibrator 515, as shown in FIG. 1, that allows vibrations to pass through the container into the fluid/aggregate system at or around the acoustic slow wave frequency. A control system 600 is connected to piezoelectric vibrator 515 and controls the frequency output of piezoelectric vibrator 515. Control system 600 has a user interface in which a user can input known values of the physical properties of the particle aggregates and their pore fluid. Control system 600 then calculates the second sound frequency employing the equations as discuss supra; and sends a signal to piezoelectric vibrator 515 to generate that second sound frequency.

In addition to setting the frequency of oscillation to the acoustic slow wave frequency, or making a frequency spectrum containing the acoustic slow wave frequency, it is also possible for control system 600 to use feedback control techniques to determine the acoustic slow wave frequency, and to track changes in the frequency as it changes due to aggregate breakup. If a range of ultrasound frequencies are pumped into a specimen, and the power absorption is analyzed as a function of frequency, at the acoustic slow wave frequency the power absorbed by the system will be the maximum, as shown in FIG. 3. It has been found that compressional attenuation is 90–99% due to excitation of the compressional slow wave over frequency ranges where it can occur. Normal sound wave attenuation provides only a low background power absorption over a broad frequency range compared to the high frequency-specific attenuation due to excitation of the slow wave.

The peak in the power absorption profile can be tracked by power spectrum analysis techniques, and the excitation spectrum changed to follow the time-varying demands of the system (e.g., as new aggregates are added, as flow rates vary, etc.).

As shown in FIG. 3, the power absorption at the peak of the power absorption frequency spectrum (i.e., the slow wave frequency) is proportional to the concentration of aggregates in the sample. As discussed above, this power absorption is almost entirely due to slow wave excitation in aggregates. Power absorption by normal sound excitation is smaller by 1–2 orders of magnitude. Also noted in FIG. 3 is the dependence of the power absorption-concentration curve on the shape of the pores in the aggregate. For pores between spherical particles the slope of the curve is lower than for pores between long flat particles. Thus, there is some degree of experimental calibration through the use of microscopically characterized samples that must be done if there is a distribution of particle shapes and sizes. Such calibration techniques are well known to those skilled in the art.

The present invention may be used in a number of ways. For example, an application is in the prevention of aggregation of blood cells in blood bag bank supplies to extend shelf life. FIG. 2 illustrates the acoustic slow wave frequencies required to disperse red blood cells and white blood cells that have settled under the influence of gravity in stored whole blood supplies. A container of blood or bags of whole blood can be put on a sonic stage as in FIG. 1 and acoustic slow wave frequencies can be applied, thereby keeping blood cells dispersed. While ultrasonic signals may damage blood cells via cavitation, from bubbles forming under the pressure variations of the ultrasound, the sonic frequency range of the appropriate compressional slow wave is unlikely to cause such damage. Cavitation is reduced at these low frequencies; cavitation peaks at approximately 20 kHz, and decreases exponentially above and below this frequency in water-like systems.

One can use Eq. (4) to estimate the acoustic slow wave frequency for blood serum oscillating out of phase with collections of white blood cells, red blood cells, and platelets. It is convenient to do this as a function of % S, the percent of solids by volume in a particle aggregate. In terms of % S we can determine the porosity $\phi$ (via Eq. (2)). The only other unknown variable in Eq. (4) is $S_v$, the surface area per unit volume. This is given in the discussion above for specific particle packing geometries, for example, for cubic close packing of particles, the porosity $\phi=0.476$, and $S_v=\pi/D$. Typical particle diameters D are $D_{red\ cell}=7\mu$, $D_{whitecell}=10\mu$, $D_{platelet}=1\mu$. The results of this calculation are shown in FIG. 2.

As we see in the figure, the acoustic slow wave frequencies for red (middle curve) and white blood cells (lowest curve) are quite low, below 10 kHz, over most of the reasonable ranges of percent solids (percent solids greater than 75% are unlikely to occur for largely random systems). These low frequencies are advantageous for the protection of blood cells from cavitation damage. Analysis of the Kirkwood-Bethe equation for cavitation bubble dynamics in an ultrasonic field shows that maximum cavitation occurs at around 20 kHz in water-like systems, with an overtone at around 40 kHz. By avoiding those frequencies, we can avoid much of the potential damage to red and white cell membranes.

For platelets (highest curve), the case is somewhat more complicated. In this case, the acoustic slow wave frequency extends from 15 kHz to over 50 kHz, depending on the aggregate percent solids. However, by using a notch filter that excludes the 20 kHz and 40 kHz regions we can break up many platelet aggregates and still avoid the dangers of cavitation. The ultrasonically-induced hitting of redispersed platelets against platelet aggregates in the % S zones covered by the frequency notches (40%<% S<55%) will tend to break up these aggregates.

The present invention also may be useful dispersing blood clots in situ in living patients. The simplest way to do this is to apply sound waves of the appropriate frequency by holding a sonic (or ultrasonic) transducer to the affected area of the body to break up the clot. The present invention can be a small hand-held unit as shown in FIG. 4 which includes an assembly 700 for holding transducer element next to the affected area of the body. Preferably hand held unit would be employed in conjunction with a tracking unit to prevent a problem in which a clot can start to break up and move out of the sonified zone. This clot can then stick somewhere else and cause further medical problems.

Other techniques can be employed to address the problem of moving clots, such as Doppler NMI, Doppler Ultrasound, or X-ray tomography of the veins can be employed after a radioactive dye is injected into the circulatory system. This gives an indication on how blood is flowing and clot is dispersing. These blood flow monitoring techniques can be used in conjunction with acoustic slow wave clot breakup techniques to provide adaptive blood clot management throughout a patients body. Such a system constitutes a blood flow monitoring/clot breakup system. It consists of two parts: a blood flow monitoring subsystem—to monitor blood flow through a large part of the body or the whole body. This can be done via a Doppler ultrasound scan of the body, a Doppler NMI body scan, or by an X-ray tomography of the veins after a radioactive dye is injected. This allows the doctor to see how blood is flowing. A clot breakup system is viewed as functioning by a second sound holography system. (In holography information is gathered on a surface (e.g., photographic film) by interfering a plane wave with that same plane wave scattered from a body. When the "film" is exposed to a plane wave, an image of the original scattering body is created. The system envisioned here consists of a fluid filled tank with acoustic transducers covering the surface. Any specified part of the patient's body could be exposed to ultrasonic wave which would excite a second sound wave in a blood clot (at a location specified by the blood flow monitoring system) by activating the appropriate set of ultrasonic transducers.

Having in mind the main elements of the present invention, and not wanting to be limited to theory, the present invention is believed to operate as follows: When a solid containing a fluid is subject to a sound wave, the fluid and the liquid will oscillate in the direction of propagation of the sound wave. In general, the fluid and the porous solid respond at slightly different rates. In the limit of very low frequency the porous solid and the liquid will respond completely in phase, resulting in no net motion of the fluid with respect to the porous solid. In this limit, as discussed in the paragraph above, forces within the fluid-saturated solid occur between the maximum and minimum pressure positions within the solid, located ½ wavelength apart. Since a single particle agglomerate is small compared to the size of the wavelength of the sound wave, the pressure differences within a single agglomerate are small, resulting in small forces acting to break up the particle.

As the frequency of the driving sound wave increases, the viscous fluid motion lags slightly behind that of the approximately rigid solid. This results in fluid motion through pores in the particulate solid, which in turn induces stresses on the particle-particle contact points.

As the frequency increases, the phase lag in relative motion between the solid and liquid also increases, at least up to a point. At a point called the acoustic slow wave point the motion of the solid and liquid will be 180 degrees out of phase. At this point we have the maximum amount of motion of the fluid with respect to the aggregated solid. This results in the maximum viscous stress on the adhesive bonds. If these viscous shearing forces exceed the shear strength of the adhesive bonds between particles, the aggregate will start to fall apart. Now, however, these forces tending to destroy the aggregate will occur on the interparticle length scale, not on a scale of ½ the wavelength of the sound wave in the composite fluid.

The first analysis of these different modes of fluid motion was carried out by Biot (1956a,b; 1962), and has been a topic of continuing research [see Johnson, Plona, and Kojima (1994) and references cited therein]. The acoustic slow wave mode is also sometimes called the "compressional slow wave" or just the "slow wave". These waves have been observed experimentally in a variety of porous solids, and are well-verified (Johnson, et. al., 1994).

The frequency of the acoustic slow wave mode, $f_c$, in an infinite porous solid is given by (White, 1965):

$$f_c = \eta \phi / (2\pi k \rho_f) \quad (1)$$

where $\eta$ is the fluid viscosity, $\phi$ is the aggregate porosity, k is the aggregate permeability, and $\rho_f$ is the fluid density. $\phi$ depends on the volume fraction of solids in the aggregate particle via:

$$\phi = 1 - (\% S/100) \quad (2)$$

where % S is the percent of solids in the aggregate, by volume. This expression can be easily converted to reflect porosity in terms of % S by weight.

It is obviously impossible (or at least very difficult) to directly measure the permeability of a single particle aggregate. Therefore it is preferable to predict the aggregate permeability. There are several ways in which this can be done. Variational bounds giving the upper and lower limits have been put on the permeability of particle composites. There are also phenomenological relationships between the permeability and related quantities such as aggregate porosity. For this analysis we make use of the Carmen-Kozeny equation, which has the advantage of being a physically plausible form suggested by physical arguments, with a phenomenologically determined prefactor:

$$k = B \phi^3 / \{S_v^2 (1-\phi)^2\} \quad (3)$$

where B is a constant, typically on the order of 5, and $S_v$ is the particle surface area per unit volume within the aggregate. $S_v$ will depend on the particle size and packing of the particles, and is inversely proportional to particle diameter (Williams, 1968). Several specific particle packings have been used to calculate both $S_v$ (for use in Equations (1)–(3)) and % S in FIGS. (2) and (3), using information on the packings provided in Williams (1968). For example, for cubic close packing of particles, the porosity $\phi = 0.476$, and $S_v = \pi/D$, where D is the particle diameter. For body centered cubic packing the porosity $\phi = 0.32$, $S_v = 1.30\pi/D$. For face centered cubic packing the porosity $\phi = 0.26$, and $S_v = 4\pi/D$. For random packing the porosity $\phi = 0.63$, and $S_v = 1.41 \pi/D$. This information on $S_v$, plus Equations (1) and (3) allow the compressional slow wave frequency to be estimated by:

$$f_c = \eta \{S_v^2 (1-\phi)^2\} / (2\pi B \phi^2 \rho_f). \quad (4)$$

Useful compressional slow wave frequency can be in the range between ±15% of the calculated or measured peak slow wave frequency.

In recapitulation, there is provided a method for dispersing aggregates in a liquid medium including blood the method comprising: holding aggregates in said liquid medium in a vessel; applying a predefined acoustic slow wave frequency near said vessel for separating the aggregates in said liquid medium, said applying includes selecting a type aggregates to be dispersed in said liquid medium, determining said predefined acoustic slow wave frequency of said selected aggregates. Wherein determining said predefined said acoustic slow wave frequency includes calculating said predefined said acoustic slow wave frequency by the following equation:

$$f_c=\eta\{S_v^2(1-\phi)^2\}/(2\pi B\ \phi^2\rho_f)$$

Where $f_c$ is the acoustic slow wave frequency, $\eta$ is the fluid viscosity, $S_v$ is the primary particle surface area per unit volume of the aggregate, $\phi$ is the aggregate porosity, $\rho_f$ is the fluid viscosity, and B is a phenomenological constant.

The aggregates include red blood cells, white blood cells or platelets.

The method further comprising determining and applying a second predefined acoustic slow wave frequency as said primary particle surface area per unit volume of the aggregate changes. And, repeating said determining and applying steps until said primary particle surface area per unit volume of the aggregates reaches a selected primary particle surface area per unit volume of the aggregates.

It is, therefore, evident that there has been provided, in accordance with the present invention fully satisfies the aims and advantages hereinbefore set forth. While this invention has been described in conjunction with one embodiment thereof, it is evident that many alternatives, modifications and variations will be apparent to those skilled in the art. Accordingly, it is intended to embrace all such alternatives, modifications and variations as they fall within the spirit and broad scope of the appended claims.

What is claimed is:

1. A method for dispersing aggregates in a liquid medium including blood the method comprising:

holding aggregates in said liquid medium in a vessel; and applying a predefined acoustic slow wave frequency near said vessel for separating the aggregates in said liquid medium, said applying includes selecting a type aggregates to be dispersed in said liquid medium, determining said predefined acoustic slow wave frequency of said selected aggregates, determining said predefined said acoustic slow wave frequency includes calculating said predefined said acoustic slow wave frequency by the following equation:

$$f_c = \eta \{S_v^2(1-\phi)^2\}/(2\pi B \ \phi^2 \rho_f)$$

Where $f_c$ is the acoustic slow wave frequency, $\eta$ is the fluid viscosity, $S_v$ is the primary particle surface area per unit volume of the aggregate, $\phi$ is the aggregate porosity, $\rho_f$ is the fluid density and B is a phenomenological constant.

2. The method of claim 1, wherein said aggregates include red blood cells, white blood cells or platelets.

3. The method of claim 1, further comprising determining and applying a second predefined acoustic slow wave frequency as said primary particle surface area per unit volume of the aggregate changes.

4. The method of claim 3, further comprising repeating said determining and applying steps until said primary particle surface area per unit volume of the aggregates reaches a selected primary particle surface area per unit volume of the aggregates.

5. A method for dispersing aggregates in a blood bag the method comprising:

placing said blood bag adjacent to a vibrating member;

applying a signal to said vibrating member so that said vibrating member generates a predefined acoustic slow wave frequency near said blood bag for separating the aggregates therein, said applying includes selecting a type aggregates to be dispersed in said blood bag, determining said predefined acoustic slow wave frequency of said selected aggregates.

6. The method of claim 5, wherein determining said predefined said acoustic slow wave frequency includes calculating said predefined said acoustic slow wave frequency by the following equation:

$$f_c = \eta \{S_v^2(1-\phi)^2\}/(2\pi B \ \phi^2 \rho_f)$$

Where $f_c$ is the acoustic slow wave frequency, $\eta$ is the fluid viscosity, $S_v$ is the primary particle surface area per unit volume of the aggregate, $\phi$ is the aggregate porosity, $\rho_f$ is the fluid density and B is a phenomenological constant.

7. The method of claim 5, wherein said aggregates include red blood cells, white blood cells or platelets.

8. The method of claim 6, further comprising determining and applying a second predefined acoustic slow wave frequency as said primary particle surface area per unit volume of the aggregate changes.

9. The method of claim 8, further comprising repeating said determining and applying steps until said primary particle surface area per unit volume of the aggregates reaches a selected primary particle surface area per unit volume of the aggregates.

10. The method of claim 7, wherein said predefined acoustic slow wave frequency is substantially lower than cavational frequency of said aggregates.

11. A method for dispersing blood clots aggregates in a blood bag, the method comprising:

placing a vibrating member adjacent to said blood clots aggregates;

applying a signal to said vibrating member so that said vibrating member generates a predefined acoustic slow wave frequency near said blood clots aggregates for separating the aggregates, said applying includes selecting a type aggregates to be dispersed, determining said predefined acoustic slow wave frequency of said selected aggregates.

12. The method of claim 11, wherein determining said predefined said acoustic slow wave frequency includes calculating said predefined said acoustic slow wave frequency by the following equation:

$$f_c = \eta \{S_v^2(1-\phi)^2\}/(2\pi B \ \phi^2 \ \rho_f)$$

Where $f_c$ is the acoustic slow wave frequency, $\eta$ is the fluid viscosity, $S_v$ is the primary particle surface area per unit volume of the aggregate, $\phi$ is the aggregate porosity, $\rho_f$ is the fluid density and B is a phenomenological constant.

13. The method of claim 11, wherein said aggregates include red blood cells, white blood cells or platelets.

14. The method of claim 12, further comprising determining and applying a second predefined acoustic slow wave frequency as said primary particle surface area per unit volume of the aggregate changes.

15. The method of claim 12, further comprising repeating said determining and applying steps until said primary particle surface area per unit volume of the aggregates reaches a selected primary particle surface area per unit volume of the aggregates.

16. The method of claim 13, wherein said predefined acoustic slow wave frequency is substantially lower than cavational frequency of said aggregates.

17. The method of claim 11, further comprising tracking said aggregates as said aggregates move beyond a predefined zone.

* * * * *